United States Patent [19]

Agrawal et al.

[11] Patent Number: 5,109,126
[45] Date of Patent: Apr. 28, 1992

[54] 5'[2'(3')-O-(2,4,6-TRINITROPHENYL) PYPRIMIDINE NUCLEOSIDE]DIPHOSPHATE 1-GLYCOSIDES

[75] Inventors: Sudhir Agrawal, Shrewsbury; Richard A. Cardullo, Wollaston; David E. Wolf, Hudson, all of Mass.

[73] Assignee: Worcester Foundation for Experimental Biology, Mass.

[21] Appl. No.: 280,597

[22] Filed: Dec. 6, 1988

[51] Int. Cl.$^5$ .......................... C07H 19/10
[52] U.S. Cl. ...................... 536/29; 536/27; 536/28; 536/18.6; 536/6; 536/55.2; 536/123; 435/6
[58] Field of Search ......................... 536/29

[56] References Cited

U.S. PATENT DOCUMENTS 3,687,932  8/1972  Nakamachi et al. ............... 536/29
4,472,572  9/1984  Shizuya ........................... 536/27
4,704,361  11/1987 Miccoli et al. ................... 435/188

FOREIGN PATENT DOCUMENTS 3824384  11/1963  Japan .
3824385  11/1963  Japan .

OTHER PUBLICATIONS

Hiratsuka et al., Biochimica et Biophysica Acta, 320, 635–647 (1973).
Michelson et al., J. Chem. Soc., 3459–3463 (1956).
Jacobson et al., Biochemistry, 22, 4247–4257 (1983).
Berman, J. Biol. Chem., 261(35), 16494–16501 (1986).
B. D. Shur and S. Roth, "Cell Surface Glycosyltransferases", Biochim. Biophys. Acta, 415:473–512 (1975).
Schwyzer, M. and R. L. Hill, J. Biol. Chem. 252:2338–2345 (1977).
E. G. Moczydlowski and P. A. George Fortes, J. Biol. Chem., 256:2357–2366 (1981).
Cardullo, R. A. et al. Abstract: Annual Meeting of Soc. of Cell Biology, 1988.

Primary Examiner—Johnnie R. Brown
Assistant Examiner—L. Eric Crane
Attorney, Agent, or Firm—Hamilton, Brook, Smith & Reynolds

[57] ABSTRACT

A method of assaying, detecting, monitoring, and influencing in vitro and in vivo activity of glycosyltransferase and sugar nucleotides which are analogs of the naturally-occurring sugar nucleotides for which the glycosyltransferases are specific. These sugar nucleotide analogs include those labeled with a fluorogenic moiety at the 2' or 3' position of the ribose or at another location (e.g., on a constituent phosphate or in the nucleotide backbone), such as the UDP-galactose analog, 2'(or 3')-O-(2,4,6-trinitrophenyl)-5'-uridine diphosphate galactose (TUG). A highly specific assay for soluble glycosyltransferase has been developed which utilizes the fluorogenic sugar-nucleotide analogs. These assays rely on changes in spectral properties resulting from specific binding events of the sugar nucleotide analog and the glycosyltransferase. Assays of this invention do not rely on the use of radio-isotopes and can be used to assess glycosyltransferase activity in living cells.

2 Claims, 7 Drawing Sheets

β-L-Fucose
(Fuc)

β-D-Galactose
(Gal)

β-D-N-Acetylgalactosamine
(GalNAc)

β-D-N-Acetylglucosamine
(GlcNAc)

β-D-Mannose
(Man)

Sialic acid
(N-Acetylneuraminate)
(Sia)

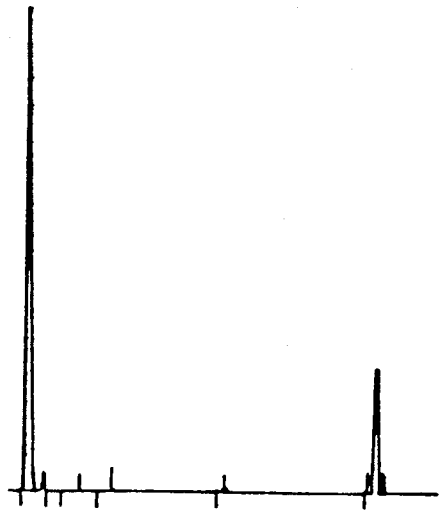
FIG. 7A
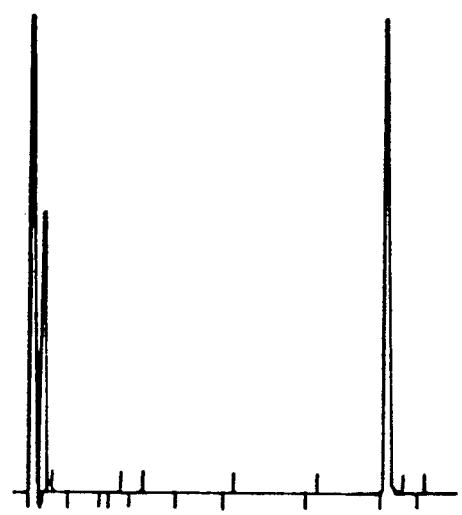
FIG. 7B
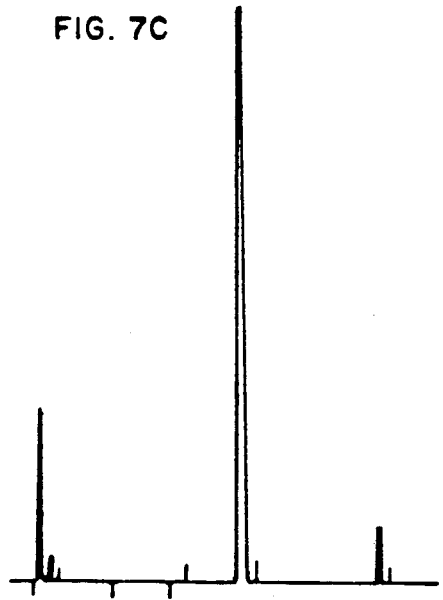
FIG. 7C
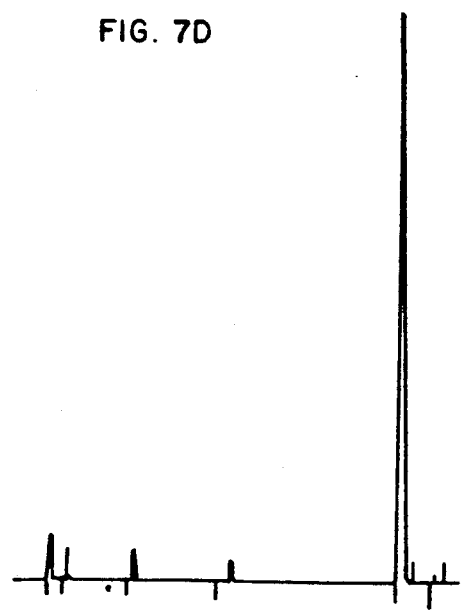
FIG. 7D
FIG. 7

5'[2'(3')-O-(2,4,6-TRINITROPHENYL) PYPRIMIDINE NUCLEOSIDE]DIPHOSPHATE 1-GLYCOSIDES

FUNDING

Work described herein was funded by grants from the National Institutes of Health.

BACKGROUND

Glycosyltransferases catalyze transfer of a monosaccharide residue from a sugar nucleotide (sugar donor) to the non-reducing terminus of a specific sugar acceptor. This process occurs within cells, especially in the Golgi apparatus, and is involved in the synthesis of all of the known complex carbohydrates, including glycoproteins, glycolipids and glycosaminoglycans. The reaction is represented in FIG. 1, in which different monosaccharides are represented by different shapes. (Taken from Roth, S. et al., *Cell and Tissue Interactions*, pp 209-223, ed. J. W. Lash and M. M. Burger, Raven Press, 1977.)

FIG. 1 depicts a trisaccharide sugar acceptor linked at its reducing end to a protein or lipid moiety, which is represented by a wavy line. A glycosyltransferase, represented as "enzyme", catalyzes the transfer of a monosaccharide from a glycosyl donor (sugar-nucleotide phosphate donor) to the nonreducing terminus of the sugar acceptor. This reaction involves a cofactor, which is generally a divalent cation (e.g., $Mn^{2+}$) In the reaction products are a tetrasaccharide and a free nucleotide.

Such reactions are carried out within cells to effect the addition of monosaccharides to a glycosylated (carbohydrate-containing) substrate, such as glycoproteins, glycolipids, and proteoglycans. The reactions occur in the Golgi apparatus and are catalyzed or directed by a glycosyltransferase which is specific not only for the sugar-nucleotide substrate (for the monosaccharide to be transferred), but also for the specific carbon atom of the sugar or amino acid acceptor involved. For example, one glycosyltransferase catalyzes the transfer of N-acetylneuraminic acid (sialic acid) from CMP-sialic acid only to the 3 carbon atom galactose and a second catalyzes transfer only to the 6 carbon atom. Darnell, J. et al., *Molecular Cell Biology*, p. 958, Scientific American Books (1986). These transferases are named according to the sugar donors they utilize. For example, all galactosyltransferases transfer galactose from uridine diphosphate galactose to their specific acceptors, while neuraminyltransferase (sialyltransferase) transfers N-acetyl neuraminic acid (sialic acid) from its cytidine monophosphate derivative (CMP-Neu) to the required acceptor. As far as is known, no transferase can use more than one type of sugar donor. B. D. Shur and S. Roth, *Biochim. Biophys. Acta* 415:473-512 (1975).

Recently, it has been found that glycosyltransferases are present on cell surfaces, as well as within cell organelles, such as Golgi apparatus, endoplasmic reticula and mitochondrial membranes. B. D. Shur and S. Roth, *Biochim. and Biophy. Acta* 415:473-512 (1975) and references cited therein.

Evidence suggests that on cell surfaces, glycosyltransferases participate in a myriad of cellular interactions by binding their specific carbohydrate substrates on adjacent cells or in the extracellular matrix. It has been shown that if a cell surface glycosyltransferase molecule comes in contact with an appropriate acceptor (e.g., a glycoprotein) on another cell, the glycosyltransferase will bond non-catalytically with the acceptor. Thus, there will be an initial adhesive recognition as the result of creation of a transferase-substrate complex. In the extracellular environment, there are no sugar-nucleotides and cofactor concentrations are well below those needed for glycosyltransferase activity; thus, there is no enzymatic activity. Addition of the appropriate sugar-nucleotide and co-factor at appropriate levels has been shown to result in enzymatic addition of monosaccharide to acceptor (glycosylated substrate); glycosyltransferases present cease to act as cell adhesion molecules. Surface glycosyltransferases play a role in embryonic cell adhesion and migration, embryogenesis, immune recognition, growth control B. S. Shur, *Mol. Cell. Biochem.* 61:143-158 (1984).

For example, galactosyltransferase in sperm heads, which catalyzes the transfer of galactose from uridine 5'-diphosphate galactose to terminal N-acetylglucosamine residues, may recognize and bind to specific N-acetylglucosamine residues on the egg zona pellucida. P. M. Wassarman, *Science*, 235:553 (1987). Recognition and binding are accomplished through formation of an enzyme-substrate complex.

Presently, assessment of glycosyltransferase activity or function typically relies on use of sugar-nucleotides which are isotopically labeled at the monosaccharide (e.g., $^3H$ or $^{14}C$) or monitoring of the release of hydrolyzed nucleotide spectrophotometrically. For example, most studies of cell surface glycosyltransferase activity rely on the addition of sugar nucleotides that are isotopically labeled at the monosaccharide. See Schwyzer, M. and R. L. Hill, *J. Biol. Chem.*, 252:2338-2345 (1977). However, assays of this kind must control for the potential intracellular utilization of free labeled sugars which result from nucleotide hydrolysis by sugar phosphatase and nucleotide pyrophosphatases. Shur, D. B., *Mol. Cell. Biochem.* 61:143-158 (1984). These radioassays, in addition, are cumbersome and time-consuming.

Immunometric methods have also been developed for localization of cell surface glycosyltransferases. Anti-glycosyltransferase antibodies directed against the soluble form of the enzyme have been used to localize cell surface glycosyltransferase activity. However, use of these antibodies is limited because the anti glycosyltransferases are not very pure and their use generally disrupts the cell adhesion functions of glycosyltransferase. Phototungstic acid has also been used to visualize and localize glycosyltransferases. However, it can be used only with high molecular weight acceptor molecules and works poorly with the acid labile sialytransferases. See Schachter, H. and S. Roseman, "Mammalian Glycosyltransferases", pp 85-160 in: *The Biochemistry of Glycoproteins and Proteoglycans*, (ed. W. J. Lennarz), Plenum Press, 1980.

It would be useful to have a method of detecting glycosyltransferases and/or monitoring their activity which does not rely on the use of radio isotopes. Such a method would be particularly valuable if it made detection and/or monitoring of such enzymes in living cells.

SUMMARY OF THE INVENTION

The present invention relates to methods of assaying, detecting, monitoring and influencing (i.e., enhancing or inhibiting) glycosyltransferase activity in vitro and in vivo, through the use of sugar-nucleotides which are analogs of the naturally-occurring sugar-nucleotides for which glycosyltransferases are "specific", either in that they 1) catalyze specifically transfer of the monosaccharide contained in the sugar-nucleotide to an appropriate glycosylated acceptor or 2) bind specifically to an appropriate acceptor bound to the surface of another cell.

The present invention also relates to such analogs, referred to as sugar-nucleotide analogs, which are sugar nucleotides which have been modified fluorescently and retain their ability to act as substrates for their specific glycosyltransferase. In particular, the sugar-nucleotide analogs of the present invention are fluorogenically-labeled sugar-nucleotide analogs in which the nucleotides are labeled at the 2' or 3' position of the ribose or at another location (e.g., on a constituent phosphate or in the nucleotide backbone). One such sugar-nucleotide analog, which is useful in the present method, is the UDP-galactose analog, 2' (or 3')-0-(2,4,6-trinitrophenyl)-5'-uridine diphosphate galactose (TUG) (FIGS. 3 and 4). This compound is a fluorescent analog of UDP-galactose which has been shown to undego a fluorescent shift when it is bound to galactosyltransferase and to specifically label galactosyltransferase sites on mouse spermatozoa.

A highly specific assay for soluble glycosyltransferase has been developed; in the assay, a sugar-nucleotide analog, such as TUG is incubated with the appropriate glycosyltransferase (i.e., galactosyltransferase). Under appropriate conditions, the interaction of TUG and glycosyltransferase results in changes in spectral properties which serve as the basis for detecting specific binding events of the sugar-nucleotide analog and the glycosyltransferase. This highly specific assay does not rely on the use of radio-isotopes and can be used to assess glycosyltransferase activity in living cells.

Compositions and detection/assay methods of this invention are useful for detecting and localizing glycosyltransferase activity within cell organelles (e.g., Golgi apparatus) and on cell surfaces. In addition compositions of this invention can be used to influence fertilization by altering (enhancing or inhibiting) the binding of egg and sperm through alteration of binding of sperm head glycosyltransferase with its appropriate receptor on the egg zona pellucida. For example, a sugar-nucleotide (such as uridine diphosphate galactosidase), can be affixed to the surface of a condom or vaginal insert and be used to block sperm-egg binding by causing sperm head glycosyltransferase to bind to the condom or vaginal insert. A sugar-nucleotide used for this purpose can be modified or unmodified. For example a sugar-nucleotide analog which is a sugar-nucleotide modified (e.g., by replacing oxygen present in constituent sulfur) in such a manner as to render the analog noncleavable.

BRIEF DESCRIPTION OF FIGURES

FIG. 7 shows the results of a liquid chromatographic assay of the product of the reaction shown in FIG. 3. The product (TUG) has a retention time of about 23.6 minutes and the reagent (labeled as DYE) elutes as a separate peak.

DETAILED DESCRIPTION OF THE INVENTION

This invention is based on the discovery that modification of a sugar-nucleotide at the 2' or the 3' position of its constituent ribose results in production of a sugar-nucleotide analog which is a fluorescent substance which undergoes a fluorescent shift when it is bound to its specific soluble glycosyltransferase. The sugar-nucleotide analog, when bound in this manner, specifically attaches a label useful for detecting glycosyltransferases on cell surfaces and glycosyltransferase-catalyzed reactions within cells. The present invention relates to novel fluorogenic sugar-nucleotide analogs, methods of making these analogs, and uses therefor. The invention also pertains to use of these sugar-nucleotides and sugar-nucleotide analogs to influence mammalian fertilization and to compositions useful for this purpose.

FLUOROGENIC SUGAR-NUCLEOTIDE ANALOGS

Figure 1:
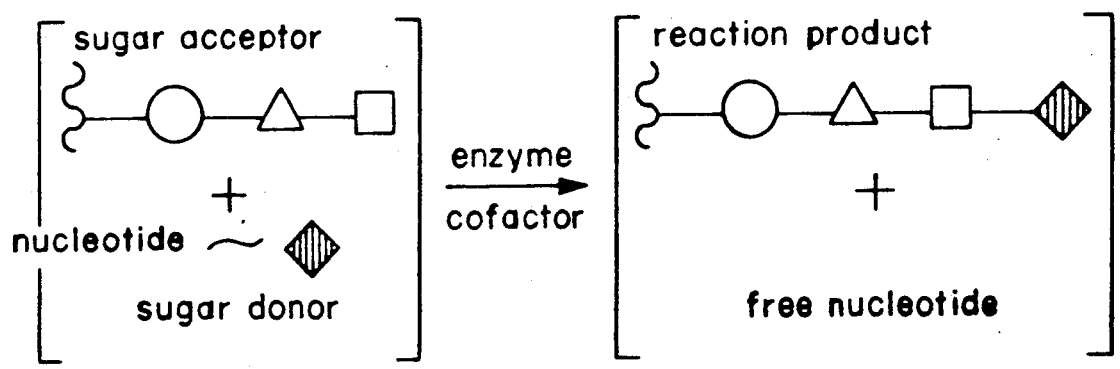
FIG. 1 is a schematic representation of glycosyltransferase-catalyzed transfer of a monosaccharide from a sugar-nucleotide to a glycosylated sugar-acceptor.

The sugar-nucleotide analogs of this invention are fluorogenic sugar-nucleotides capable of acting as a glycosyl donor in the glycosyltransferase-catalyzed synthesis of glycosylated substances, such as glycoproteins. The general reaction scheme for monosaccharide transfer catalyzed by glycosyltransferase enzymes, as it occurs in cells, is represented in FIG. 1. As shown, the sugar-donor is a sugar-nucleotide complex and the sugar-acceptor is a carbohydrate-containing (glycosylated) molecule. Transfer of the sugar moiety, through the action of an appropriate glycosyltransferase, results in addition of the monosaccharide from donor to acceptor and production of free nucleotide. The acceptor molecule can be any glycosylated substance or molecule, such as glycopeptides, glycoproteins glycolipids and proteoglycans.

Sugar-nucleotide analogs of the present invention serve as substrates (sugar-donors) for glycosyltransferase reactions. Because the sugar-nucleotide analogs are fluorescently labeled and are added with great specificity to an acceptor, they are used to selectively label an active site of the glycosyltransferase molecule.

Figure 4:
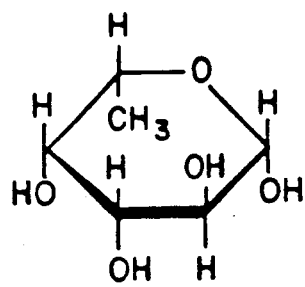
FIG. 4 shows the structural formulae of sugar moieties of sugar-nucleotide analogs of the present invention.
Figure 4:
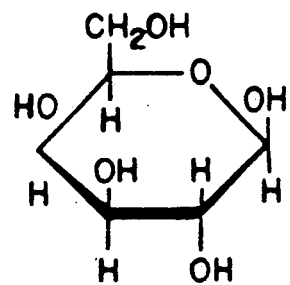
Figure 4:
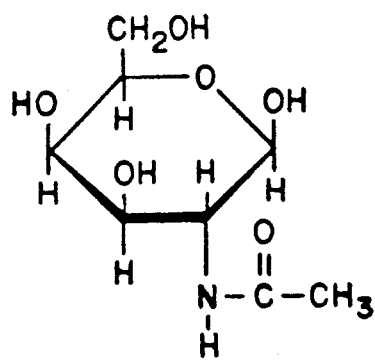
Figure 4:
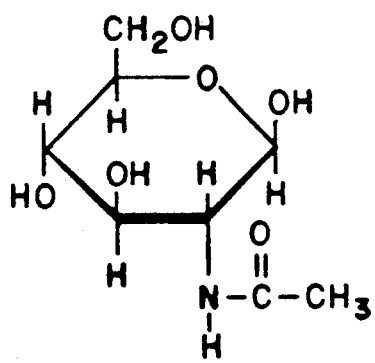
Figure 4:
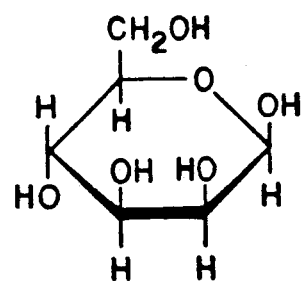
Figure 4:
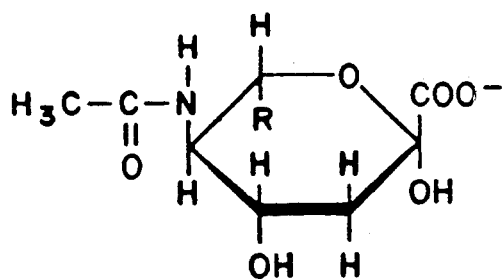

In the sugar nucleotide analogs, the sugar-phosphate linkage involves the anomeric carbon of the sugar (C-1 of D-glucose, D-galactose, D-mannose, L-fucose, N-acetyl-D-glucosamine, N-acetyl-D-galactosamine and C-2 of sialic acid). The structural formulas of the sugar moieties of sugar-nucleotide analogs of this invention are represented in FIG. 4.

A sugar-nucleotide, to which a fluorogenic moiety is added by the method of the present invention to produce sugar-nucleotide analogs can be represented by the formula:

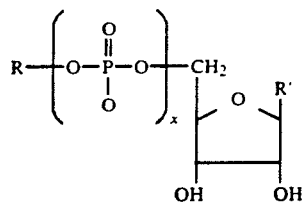

in which R' is a pyrimidine or purine radical (e.g., radical forms of uracil, thymine, cytosine, 5-methylcytosine, adenine or guanine). See H. R. Mahler and E. H. Cordes, *Biological Chemistry*, Harper and Row, 1966, incorporated herein by reference. R is a glycosyl radical of alpha or βeta linkage, such as those whose structural formulae are represented in FIG. 4. For example, R can be the β-L-fucosyl, β-D-galactosyl, β-D-N-Acetylgalactosaminyl, β-D-acetylglucosaminyl, β-D-mannosyl, and sialyl radicals.

Figure 2:
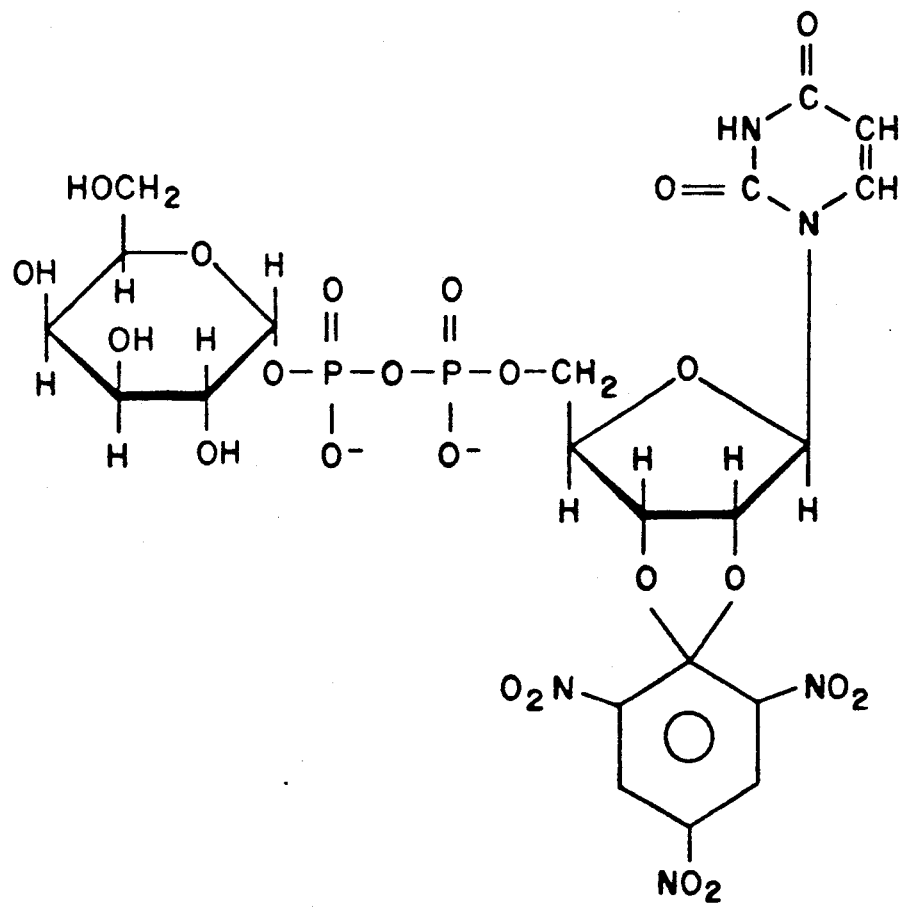
FIG. 2 shows the structural formula of 2'(or3')-0-(2,4,6-trinitrophenyl) uridine diphosphate galactose (TUG).
Figure 3:
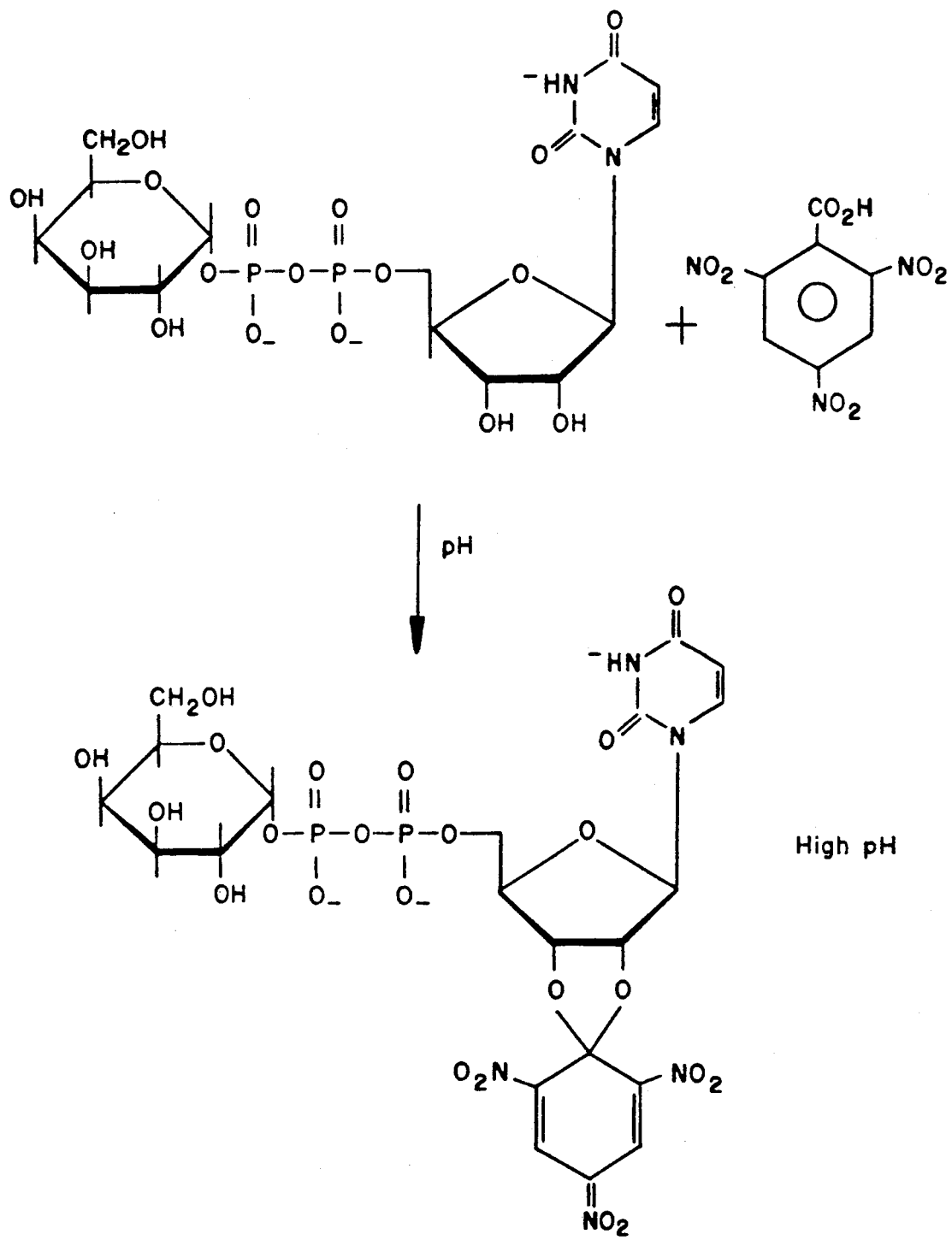
FIG. 3 shows the reaction of trinitrobenzosulfonic acid (TNBS) with uridine diphosphate (UDP) galactose to form TUG.

A sugar-nucleotide analog, such as 2' (or 3')-0-2,4,6-trinitrophenyluridine diphosphate galactose (or TUG) is fluorescent. Production of this analog is described in detail in Example 1. In this case, uridine diphosphate galactose (UDP) was reacted with trinitrobenzosulfonic acid (TNBS), under the conditions described, to produce TUG. It is to be understood that this same method can be used, with appropriately-selected reactants to label other sugar-nucleotides and produce other sugar-nucleotide analogs useful for assessment of glycosyltransferase activity and function As described in Example 1, TUG was prepared by modifying the sugar-nucleotide UDP-galactose through reaction with TNBS. The resulting analog was purified, using HPLC and TLC. The purified compound has an absorbance profile clearly distinct from that of either of the reactants (UDP-gal. TNBS). At neutral and basic pH, the product exhibits absorbance maxima at 260 nm, 408 nm and 453 nm. As the solution becomes acidic (pH<7), the absorbance values between 400 nm and 500 nm decrease in a pH dependent fashion. By monitoring the absorbance at 408 nm as a function of pH, a titration curve can easily be constructed. These absorbance properties are indicative of a chemical structure known as the Meisenheimer complex (Foster et al., *Red. Trav. Chim. Pay Bas* 84:516-520 (1965) and suggest that the structure of the product is as shown in FIGS. 2 and 3. Under acidic conditions, the ether linkage between the 2' (or 3')-end of the ribose and the 1 position of the trinitrobenzene is hydrolyzed, yielding a loss in both absorbance and fluorescence characteristics.

TUG also exhibits some interesting fluorescent and useful properties. In the absence of soluble glycosyltransferase (galactosyltransferase), TUG's excitation spectrum is similar to its absorbance spectrum with a corresponding emission maximum at 540 nm (yellow/green). In the presence of galactosyltransferase, the fluorophore shows an additional excitation maxima at 360 nm, with an emission from 440 nm to 470 nm (blue/violet). This change in spectral properties make its possible to determine specific binding events of TUG to galactosyltransferase.

The sugar-nucleotide analog represented in FIG. 2, which is particularly useful for detecting specific binding with galactosyltransferase, is the TNBS derivative of uridine 5'-diphosphate galactose.

The method of the present invention can be used for producing other fluorogenic derivatives of other sugar nucleotides useful for detecting specific binding to their respective glycosyltransferases. For example, if fucosanyltransferase activity is to be assessed, a sugar-nucleotide analog, such as modified TNP-TGP-fucose, can be produced and used as described above for galactosyltransferase. Alternatively, if sialyltransferase activity is to be assessed, a sugar-nucleotide analog whose components include cytidine monophosphate and sialic acid can be produced and used.

Generally, fluorogenic sugar-nucleotide analogs of this invention are formed by attaching 2,4,6-trinitrobenzene sulfonic acid, or other moiety which can form a Meisenheimer complex, to a sugar-nucleotide, using known techniques with modification as needed (e.g., modification of the procedure of Hiratsuka and Uchida (*Biochim. Biophys. Acta* 320:635-647 (1973)). 2,4,6,-trinitrobenzene sulfonic acid or other sulfonic acid is added, under appropriate conditions (pH, temperature, time) to a sugar-nucleotide solution The reaction is allowed to proceed for sufficient time to allow labeling of the sugar-nucleotide and is monitored using known techniques (e.g., thin layer chromatography). Fractions are purified (e.g., on a Sephadex column) and eluants are monitored under UV light.

Glycosyltransferase binding assays

The fluorogenic sugar-nucleotide analogs of this invention are particularly useful for determining the presence or absence of specific binding events between a monosaccharide and its particular glycosyltransferase enzyme.

These methods make use of the unique spectral properties of the fluorogenic substrates (sugar-nucleotide analogs). As described above, the compound produced by reacting uridine-diphosphate galactose with TNBS, named TUG (2'(or 3')-0-(2,4,6-trinitrophenyl) uridine 5'-diphosphate galactose) has an absorbance profile that is clearly distinct from either of its reactants. As also described, there is a spectral shift evident when the fluorogenic sugar-nucleotide analog binds with its appropriate glycosyltransferase.

Detection of soluble glycosyltransferase enzymes in biological fluids using the present method is based on measuring the spectral shift evident when the fluorogenic substrate (e.g., TUG) comes in contact with its glycosyltransferase (e.g., galactosyltransferase). In this instance (TUG-galactosyltransferase), specific binding of enzyme and substrate leads to an enhanced emission of blue-violet light. Detection of the presence or absence of glycosyltransferase enzymes in a fluid or solution can be carried out by measuring the spectral properties of the substrate before, during and after binding of the sugar-nucleotide analog with its appropriate enzyme. The shift in spectral properties (e.g., wavelength) is indicative of the presence of glycosyltransferase. If galactosyltransferase is to be detected, TUG or other sugar-nucleotide analog which is fluorescent and able to bind to galactosyltransfersae can be used and the emitted wavelength is in the range of 440–470 nm (blue-violet).

The amount of bound enzyme can be quantified by using a series of known amounts of sugar-nucleotide analog-glycosyltransferase complex as standards. By relating the spectral properties of the unknown analog-enzyme complex to differing known amounts of the complex, the degree of binding can be quantified. Alternatively, reference can be made to a control in which the substrate (sugar-nucleotide analog) concentration remains constant and the concentration of enzyme is varied. Soluble glycosyltransferase can be detected by this method in biological fluids, such as colostrum, milk, serum, cerebrospinal fluid, cell extracts, amniotic fluid and vitreous humor (see Shur and Roth, id).

Cellular materials in a biological fluid can also be assayed for the presence of these enzymes. The cellular or other biological material can be combined with a selected fluorogenic sugar-nucleotide analog (e.g., TUG) and the mixture incubated for a sufficient time for the fluorogenic analog to bind to cell glycosyltransferase present. Localization of analog-enzyme binding sites is accomplished by subjecting the cellular material to light of a wavelength sufficient to cause the substrate to fluoresce. Light emitted from the cellular material is visualized (e.g., under a fluorescence microscope) in order to localize the sugar-nucleotide enzyme reaction to a particular cellular particle, membrane or fragment thereof. Any cellular material containing, or suspected of containing, glycosyltransferases can be used. Such materials include mammalian epididymal fluid, sperm, eggs and embryos, cell surface membranes and intracellular membranes (Golgi membranes, mitochondrial membranes, endoplasmic reticulum). Biological fluids which can be assayed using the present method include cellular extracts, milk products and semen.

The method described herein is especially useful for localizing specific cell fractions in cell lysates or extracts, such as the Golgi membranes, a cell fraction especially rich in glycosyltransferases. Cells can be disrupted using known methods (i.e., sonication, French pressure cell) and size or molecular weight fractions of the extracts or lysates can be subjected to reaction with a suitable fluorogenic substrate, such as TUG. In the presence of cellular material (e.g., Golgi membranes) containing large amounts of the enzyme, the spectral properties of TUG will be recorded as an intense blue-violet coloring of the cellular fraction containing the Golgi membrane material.

Methods and compositions described herein are also useful for altering (enhancing or inhibiting) mammalian fertilization. Methods for this purpose rely on the two properties of glycosyltransferase enzymes: 1) the ability of cell surface glycosyltransferase molecules to enter into non-catalytic reactions with carbohydrate acceptor molecules in the absence of sugar-nucleotides. This cell adhesion reaction is responsible, in large part, for the binding of galactosyltransferase found in mammalian sperm heads to oligosaccharides in the egg zona pellucida; and 2) the ability of glycosyltransferase enzymes (found in the plasma membranes surrounding the mammalian sperm head) to specifically bind to their appropriate sugar-nucleotide donor molecules.

The binding of sperm to egg can be more effectively blocked by using a contraceptive to which is affixed: a) sugar acceptor molecules (glycoproteins, glycolipids, glycosaminoglycans) or their specific binding residues; and/or b) glycosyltransferase enzymes (i.e., galactosyltransferases). Thus, to a condom or vaginal insert can be affixed a plurality of glycoproteins found in the egg zona pellucida. See P. Wassarman, *Science*, 235:553–560 (1987) and references cited therein. In the absence of sugar-nucleotide donor molecules, sperm coming into contact with the condom or vaginal insert will bind to it because of the adhesive recognition between glycosyltransferase (in sperm heads) and the sugar acceptor molecules on the contraceptive device.

Alternatively, a sugar-nucleotide donor molecule (i.e., uridine diphosphate galactose) can be affixed to the contraceptive device. In this method, glycosyltransferase enzymes found in plasma membranes of sperm heads, will perferentially bind to sugar-nucleotide donor molecules affixed to the contraceptive device.

This invention is further described in the following examples.

EXAMPLE 1

Synthesis of 2',3'-0-(2,4,6-dinitrophenyl) uridine diphosphates-galactose (TUG)

The attachment of 2,4,6-trinitrobenzene to UDP-galactose was carried out according to a modified procedure of Hiratsuka and Uchida (1973).

Exactly 5 mg of UDP galactose was dissolved in 100 ul of water and the pH was adjusted to 9.5 using 0.10M lithium hydroxide (LiOH). At the same time, 26.48 $\mu$M mmoles of trinitrobenzene sulfonic acid (TNBS) was dissolved in 100 $\mu$l of water. This TNBS solution was added dropwise to the basic UDP galactose solution and was constantly stirred over 3 hours at room temperature. The pH was immediately titrated and adjusted to 9.5 using 0.10M LiOH. The reaction was allowed to proceed for up to 4 days in the dark (although the reaction was complete after only 2 days).

Figure 5:
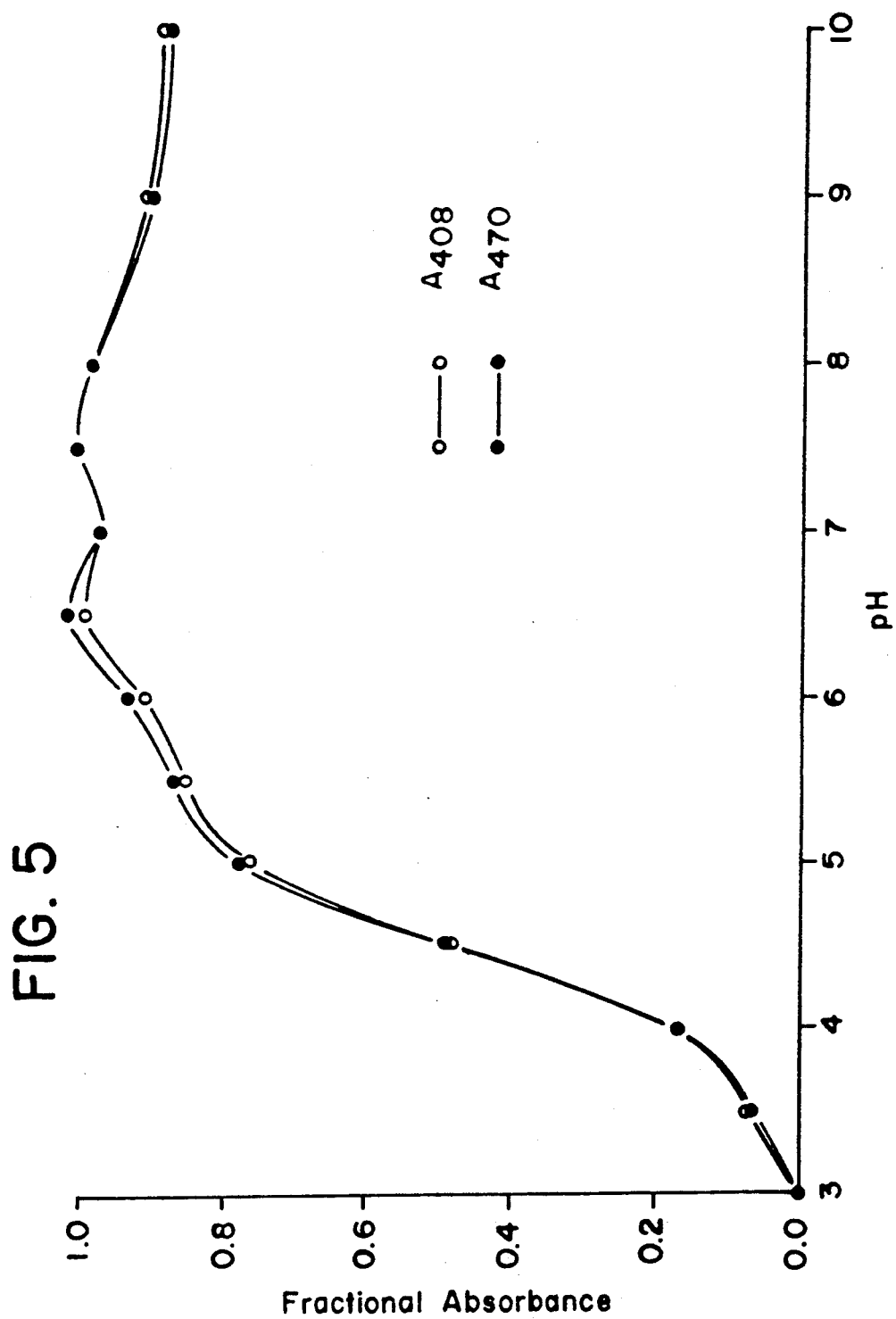
FIG. 5 shows a titration curve of TUG which depicts absorbance at two wavelengths as a function of pH.

The reaction is shown in FIG. 4. A titration curve was constructed by monitoring absorbance of TUG at 408 and 470 nm (FIG. 5).

An experiment was carried out where only galactose was allowed to react with TNBS under identical conditions as used in the TNBS reaction with uridine diphosphate galactose. No reaction was observed by TLC (data not shown).

Progress of the reaction was monitored by (thin layer chromatography) TLC using isopropanol:ammonia:water (55:10:35 or 40:10:20 v/v). Fractions were spotted on a thin layer chromatographic plate and the product band was scraped out, extracted with 25% (v/v) ethanol:water, centrifuged for 10 minutes and lyophilized. Although all spots were visible under UV light, only the product exhibited any fluorescence.

Fractions were purified on a Sephadex G-10 column. For a 5 mg scale, the bed volume (25 cm × 1/5 cm) was equilibrated with 20% (v/v) ethanol:water. The reaction mixture was loaded onto the column and fractions eluted with 20% (v/v) ethanol:water (flow rate about 1 ml min$^{-1}$). Peaks were monitored by UV light. Three peaks were eluted: 1) a mixture of uridine diphosphate (UDP), uridine diphosphate galactose (EDP-gal) and traces of product (TUG); 2) 90% of product plus TNBS+UDP-gal; and 3) TNBS+some product.

Fractions from the Sephadex column were also analyzed by reversed phase liquid chromatography (RPLC). Two buffers were used, 100 mM ammonium acetate (Buffer A) and a mixture (v/v) of 20% A and 80% CH$_3$CN (Buffer B). Flow was 2 ml min$^{-1}$. The product (TUG) eluted with a retention time of about 23.6 minutes, the hydrolyzed TNBS (i.e., trinitrobenzene) had a retention time of 13.9 minutes (FIG. 7). The UDP-gal possibly eluted with the injection peak.

Figure 6:
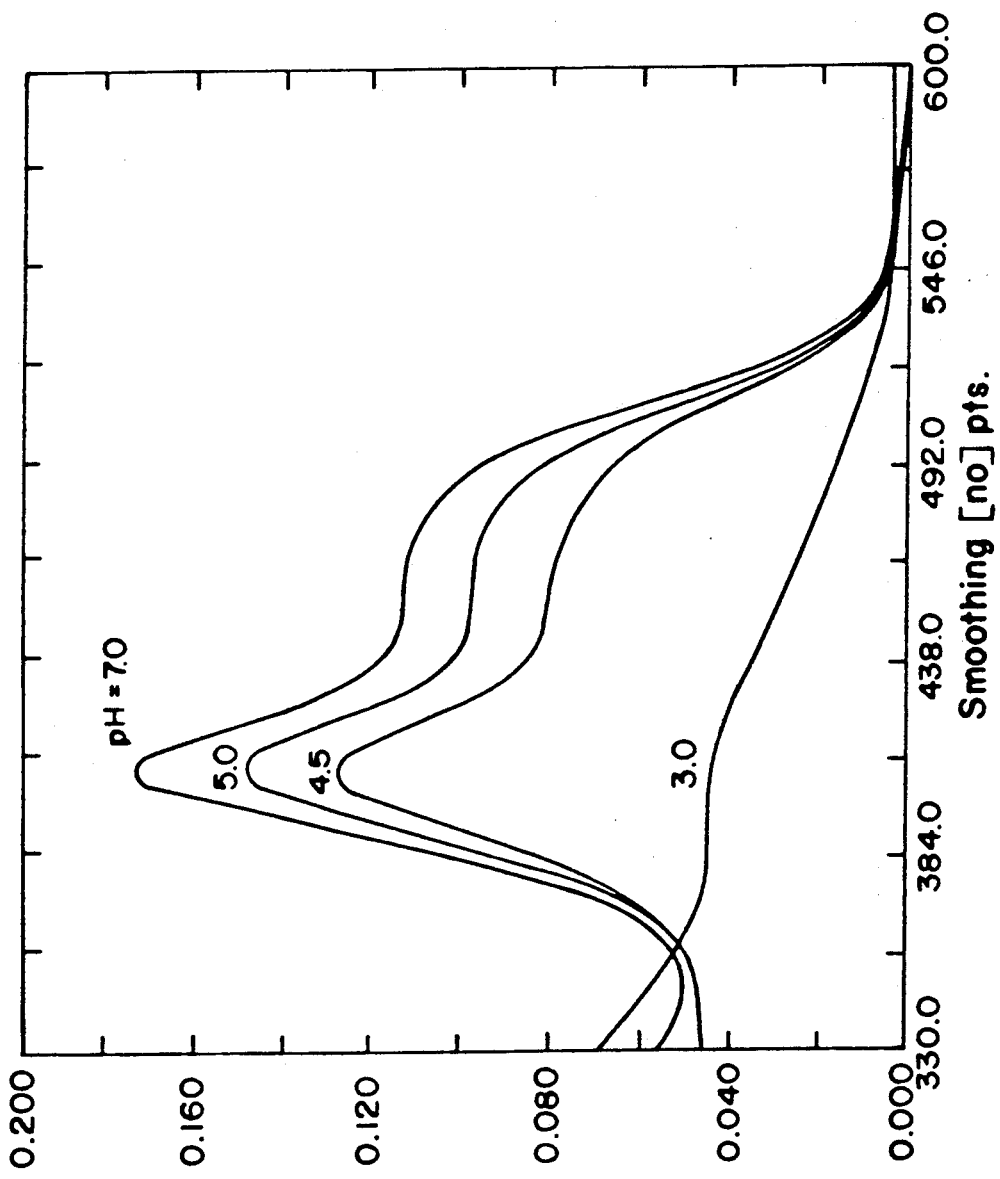
FIG. 6 shows the absorbance spectra (330–600 nm) of TUG as a function of pH.

TUG purified by HPLC and TLC was characterized. In solution, the absorbance properties of TUG were pH dependent (FIG. 6), TUG has absorbance maxima at 260 nm, 408 nm, and 453 nm with an isobestic piont at 353 nm and fluorescence excitation maxima at 353 nm and 408 nm. When soluble glycosyltransferase was added to the suspension, the excitation maximum shifted to 472 nm, with a corresponding emission maximum at 547 nm.

EXAMPLE 2

Cell labeling of mouse sperm for glycosyltransferases

Mouse spermatozoa are known to exhibit cell surface glycosyltransferases as determined by both enzymatic and fluorescent methods.

This Example illustrates that mouse sperm can be labeled with TUG, thereby identifying the galactosyltransferase (GalTase) by binding to one of its active sites. About 20 μM TUG was incubated with $10^7$ sperm for 30 minutes at 37° C. in the presence of 5 mg/ml 5'-AMP (to prevent pyrophosphatase activity) in PBS. A blue-violet localization of the head was seen under 360-390 nm excitation. In addition, a yellow-green fluorescent pattern was seen over the rest of the sperm, particularly in midpiece. The blue-violet pattern over the head is consistent with the binding of TUG to glycosyltransferase while the yellow-green pattern was consistent with non-specific labeling. This pattern is similar to the pattern seen for acrosome reacted sperm.

In another experiment, approximately 200 μM TUG was incubated with $10^7$ mouse sperm, under conditions described above, and localization of binding was assessed as also described above.

We claim:

1. A sugar-nucleotide analog having the formula:

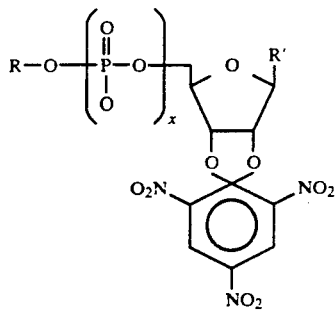

wherein R' is a pyrimidine radical selected from the group consisting of the uridyl, thymidyl, cytidyl, and 5-methylcytidyl, radicals; R is a radical selected from the group consisting of glucosyl, galactosyl, fucosyl, N-acetylgalactosaminyl, mannosyl, N-acetylglucosaminyl and sialyl radicals; and X is an integer in the range of 1–5.

2. The sugar-nucleotide analog compound 2'-0-(2,4,6-trinitrophenyl)-5'-uridine diphosphate galactose or 3'-0-(2,4,6-trinitrophenyl)-5'-uridine diphosphate galactose.

* * * * *